United States Patent
Nagashima et al.

(10) Patent No.: US 6,880,380 B2
(45) Date of Patent: Apr. 19, 2005

(54) FAILURE DIAGNOSTIC APPARATUS AND METHOD FOR AIR-FUEL RATIO DETECTING DEVICE

(75) Inventors: Satoshi Nagashima, Aichi (JP); Kenji Saito, Aichi (JP); Hidetsugu Kanao, Aichi (JP)

(73) Assignee: Mitsubishi Jidosha Kogyo Kabushiki Kaisha, Tokyo (JP)

( * ) Notice: Subject to any disclaimer, the term of this patent is extended or adjusted under 35 U.S.C. 154(b) by 0 days.

(21) Appl. No.: 10/326,998

(22) Filed: Dec. 24, 2002

(65) Prior Publication Data

US 2003/0140680 A1 Jul. 31, 2003

(30) Foreign Application Priority Data

Dec. 25, 2001 (JP) ........................................ 2001-391083

(51) Int. Cl.⁷ .......................... G01N 33/497; G01N 7/00
(52) U.S. Cl. ..................................................... 73/23.32
(58) Field of Search ............................. 73/23.31–23.32, 73/118.1, 1.06; 60/277, 297, 286, 285, 276; 436/37; 123/688, 682; 701/103

(56) References Cited

U.S. PATENT DOCUMENTS

| | | | | |
|---|---|---|---|---|
| 5,212,947 A | * | 5/1993 | Fujimoto et al. .............. 60/276 |
| 5,414,995 A | * | 5/1995 | Tokuda et al. ................. 60/276 |
| 5,423,203 A | * | 6/1995 | Namiki et al. ................. 73/1.06 |
| 5,657,627 A | * | 8/1997 | Akazaki et al. ................ 60/276 |
| 5,754,971 A | * | 5/1998 | Matsumoto et al. ......... 701/103 |
| 5,970,967 A | * | 10/1999 | Uchikawa .................... 123/688 |
| 6,135,101 A | * | 10/2000 | Konno et al. ................ 123/688 |
| 6,286,493 B1 | * | 9/2001 | Aoki ........................... 123/690 |

FOREIGN PATENT DOCUMENTS

JP        4-109445 U        9/1992

* cited by examiner

Primary Examiner—Edward Lefkowitz
Assistant Examiner—Octavia Davis
(74) Attorney, Agent, or Firm—Birch, Stewart, Kolasch & Birch, LLP

(57) ABSTRACT

A failure diagnostic apparatus for an air-fuel ratio detecting device has an exhaust emission purifying device provided in an exhaust passage; an air-fuel ratio detecting unit for detecting the air-fuel ratio of an exhaust gas from the purifying device; a first determination unit for determining that the air-fuel ratio is estimated to be rich for longer than a first predetermined period of time; a second determination unit for determining that the air-fuel ratio is estimated to be lean for longer than a second predetermined period of time; and a failure diagnosis device for determining that the air-fuel ratio detecting device has failed if a variation in the air-fuel ratio, calculated based on the detected air-fuel ratios until both the first and second determination units make the determinations, is equal to or less than a predetermined value.

11 Claims, 11 Drawing Sheets

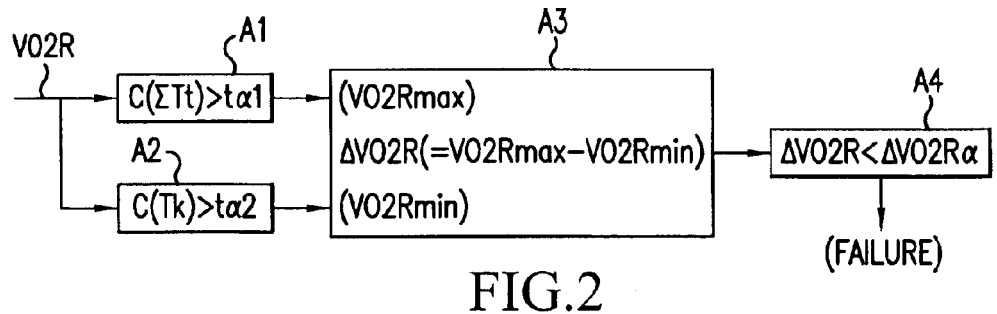
FIG.2
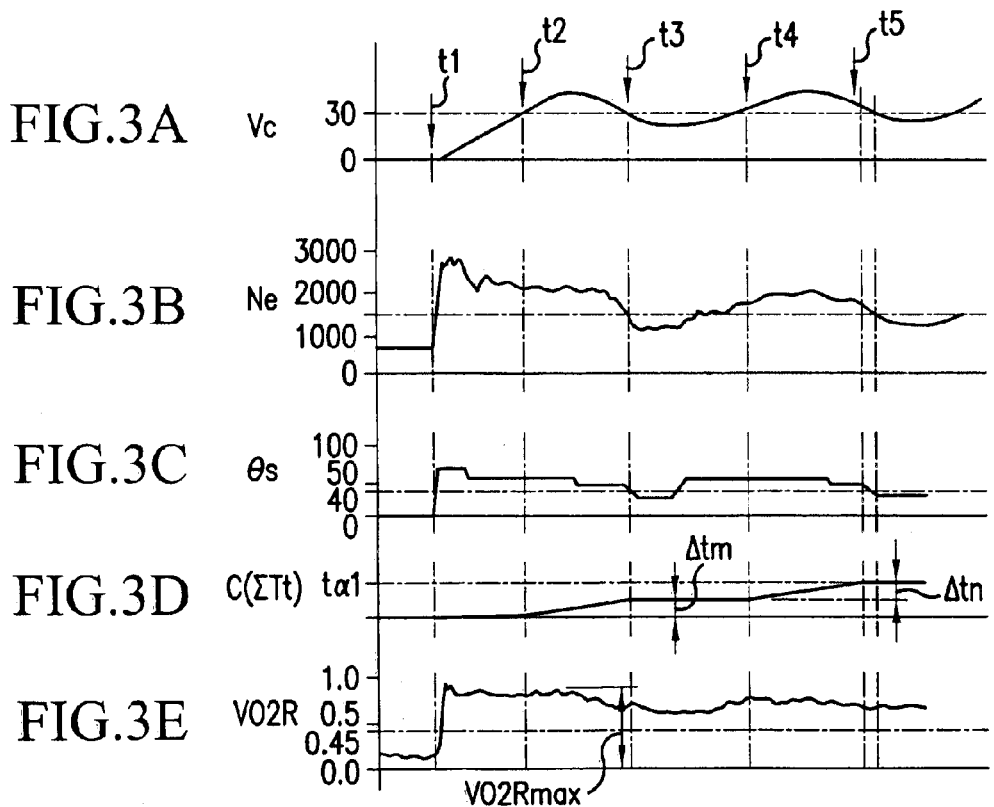
FIG.3A
FIG.3B
FIG.3C
FIG.3D
FIG.3E

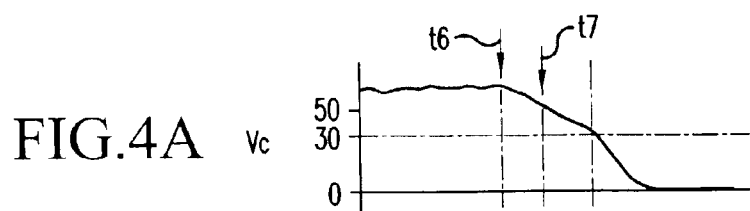
FIG.4A  Vc
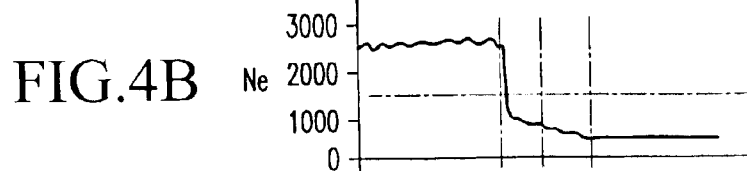
FIG.4B  Ne
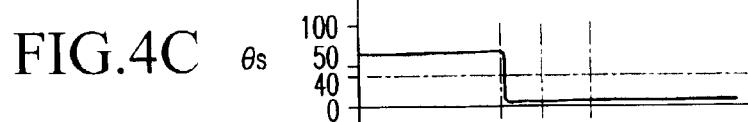
FIG.4C  θs
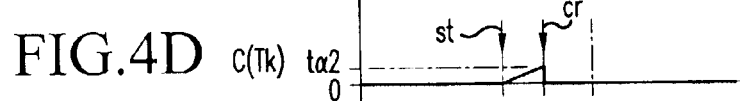
FIG.4D  C(Tk)
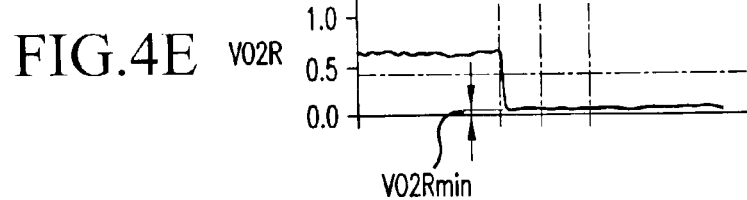
FIG.4E  VO2R
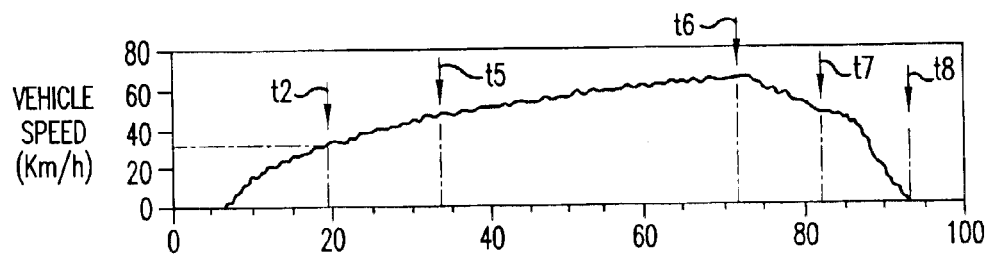
FIG.5A
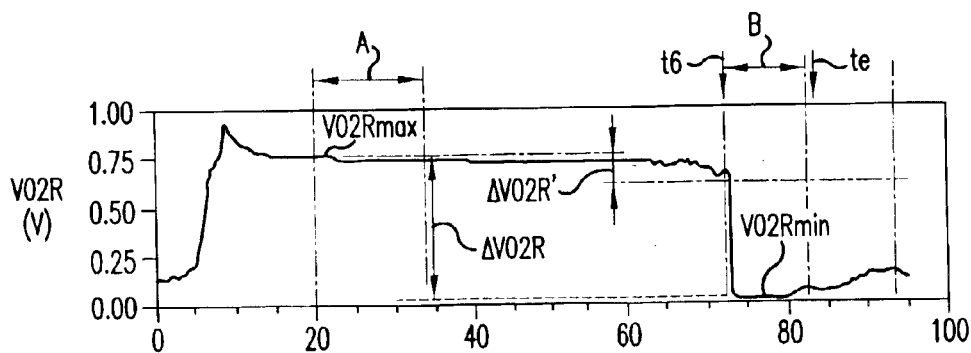
FIG.5B

FAILURE DIAGNOSTIC APPARATUS AND METHOD FOR AIR-FUEL RATIO DETECTING DEVICE

CROSS-REFERENCE TO THE RELATED APPLICATION

This non-provisional application claims priority under 35 U.S.C. §119(a) on Patent Application Serial No. 2001-391083 filed in Japan on Dec. 25, 2001, which is herein incorporated by reference.

BACKGROUND OF THE INVENTION

(1) Field of the Invention

The present invention relates to a failure diagnostic apparatus for an air-fuel detecting device for detecting air-fuel ratio of exhaust gas from an internal combustion engine and outputting air-fuel ratio information.

(2) Description of the Related Art

Conventionally, a vehicle-borne internal combustion engine is controlled in terms of an intake air volume and a fuel volume to achieve a desired operation mode selected from a group that includes a stoichiometric air-fuel ratio operation mode, a lean air-fuel ratio operation mode, a rich air-fuel ratio operation mode, a fuel cut operation mode, and so forth according to the driving condition. Further, to purify exhaust emission while the vehicle is running, an exhaust emission purifying means such as a three-way catalyst, an oxidation catalyst, or a $No_x$ catalyst is provided in an exhaust passage. Since the exhaust emission purifying device differs in activating and purifying efficiency according to the atmosphere of the exhaust gas, an air-fuel ratio sensor, as an air-fuel ratio detecting device, for detecting the air-fuel ratio of the exhaust gas is provided in the vicinity of the exhaust emission purifying device. The intake air volume and the fuel volume are controlled according to the air-fuel ratio detected by the air-fuel ratio sensor, thus maintaining a favorable exhaust emission purifying efficiency.

For this reason, if the air-fuel ratio sensor stops detecting and outputting an optimum air-fuel ratio, there is the possibility that the intake air volume and the fuel volume cannot be properly controlled due to a difference between the actual air-fuel ratio and the air-fuel ratio outputted from the air-fuel ratio sensor, causing deterioration of the exhaust gas, fuel economy, and so forth. Accordingly, it is necessary to determine whether the air-fuel ratio sensor has failed or not.

Incidentally, a conventional air-fuel ratio sensor failure diagnostic monitor determines that the air-fuel ratio sensor has failed if the air-fuel ratio sensor has outputted a value outside the range of ratios that would detect during normal driving, in other words, if the air-fuel ratio sensor outputs an impossible air-fuel ratio outside the normal detection range in the case of breaking or short circuiting. This conventional failure diagnostic monitor, which determines whether the air-fuel ratio sensor has failed or not according to whether the air-fuel ratio outputs an air-fuel ratio outside the normal detection range or not, cannot detect a failure in the air-fuel ratio sensor in the case where an output value from the air-fuel ratio sensor is stuck within the normal detection range, i.e. in the case where the air-fuel ratio outputted from the air-fuel ratio sensor is fixed at a predetermined value within the normal detection range.

To address this problem, as a device that detects deterioration of an air-fuel ratio sensor ($O_2$ sensor) disposed downstream of a three-way catalyst as an exhaust emission purifying device in an exhaust emission control system, a device is known which determines that the downstream air-fuel ratio sensor has deteriorated if, after fuel cutting (F/C) is started at a time point ta, a period of time TRL from a time point tb when an output value (R-O2) from the air-fuel ratio sensor becomes smaller than a first predetermined value (0.4 V) to a time point tc when an output value ((R-O2)) from the air-fuel ratio sensor becomes smaller than a second predetermined value (0.15 V) smaller than the first predetermined value is longer than a predetermined period of time as shown in FIG. 11.

Further, a failure diagnostic apparatus for an air-fuel ratio detecting means disclosed in Japanese Laid-Open Patent Publication (Kokai) No. 4-109445U forces the intake air-fuel ratio of an internal combustion engine to vary and detects deterioration of an air-fuel ratio sensor based on the amount of changes in the output of the air-fuel ratio sensor.

However, in the art shown in FIG. 11, since the downstream air-fuel ratio sensor is easily affected by an oxygen occluding function of the exhaust emission control system, the outputted air-fuel ratio becomes less than the first predetermined value (0.4 V) before the time point ta when the fuel cutting is started, as indicated by broken lines L1 and L2. In this state, it is impossible to determine whether the downstream air-fuel ratio sensor has failed or not. Further, when the air-fuel ratio sensor is deteriorated, there is likely to be a delay in the output value from the air-fuel ratio sensor to change, and the output value from the downstream air-fuel ratio sensor changes as indicated by a broken line L3. In this case, it is impossible to properly detect the above-mentioned period of time TRL and to determine whether the downstream air-fuel ratio sensor has deteriorated or not.

Further, the failure diagnostic apparatus for the air-fuel ratio detecting means disclosed in Japanese Laid-Open Patent Publication No. 4-109445U, which forces the air-fuel ratio of the intake air to vary, cannot promptly carry out the failure diagnosis because the operating state in which the air-fuel ratio of the intake air can be varied is restricted, and the fuel economy and the exhaust deteriorate due to the variation in the air-fuel ratio. Further, since the oxygen occluding function of the exhaust emission purifying device is not taken into consideration, an output value from the air-fuel ratio sensor, which is affected by the oxygen occluding function of the exhaust emission purifying device, does not necessarily correspond to the air-fuel ratio of the intake air, causing a wrong determination.

It is therefore an object of the present invention to provide a failure diagnostic apparatus for an air-fuel ratio detecting device, which is capable of increasing the frequency of failure diagnosis as to the air-fuel ratio detecting device to enable accurate failure diagnosis without being affected by an oxygen occluding function of an exhaust emission purifying device.

SUMMARY OF THE INVENTION

To accomplish the above object, the present invention provides a failure diagnostic apparatus for an air-fuel ratio detecting device, which determines that the air-fuel ratio detecting device has failed if it is determined that an internal combustion engine has been operated in a first operating state, in which an air-fuel ratio of exhaust in the vicinity of the exhaust emission purifying device is estimated to be rich, for a longer period of time than a first predetermined period of time and that the internal combustion engine has been operated in a second operating state, in which an air-fuel ratio of exhaust in the vicinity of the exhaust emission purifying device is estimated to be lean, for a longer period of time than a second predetermined period of time, and if a variation in the air-fuel ratio calculated based on the air-fuel ratios, which are outputted from the air-fuel ratio detecting device until it is determined that the internal combustion engine has been operated in the first operating state for a longer period of time than a first predetermined period of time and the internal combustion engine has been operated in the second operating state for a longer period of time than the second predetermined period of time, is equal to or less than a predetermined value.

BRIEF DESCRIPTION OF THE DRAWINGS

The nature of this invention, as well as other objects and advantages thereof, will be explained in the following with reference to the accompanying drawings, in which like reference characters designate the same or similar parts throughout the figures and wherein:

FIG. 2 is a block diagram showing the control arrangement of the failure diagnostic apparatus for the air-fuel ratio detecting device shown in FIG. 1;

FIGS. 3A–3E are diagrams showing functions of the failure diagnostic apparatus for the air-fuel ratio detecting means shown in FIG. 1 during accelerating from standstill, wherein FIG. 3A shows the variation of the vehicle speed Vc with time, FIG. 3B shows the variation of the engine speed Ne with time, FIG. 3C shows the variation of the throttle valve angle θs with time, FIG. 3D shows the variation of the counter value of a counter C (ΣTt) with time, and FIG. 3E shows the variation of the voltage representing the air-fuel ratio detected by a downstream $O_2$ sensor with time;

FIGS. 4A–4E are diagrams showing functions of the failure diagnostic apparatus for the air-fuel ratio detecting device shown in FIG. 1 as the running vehicle comes to a standstill, wherein FIG. 4A shows the variation of the vehicle speed Vc with time, FIG. 4B shows the variation of the engine speed Ne with time, FIG. 4C shows the variation of the throttle valve angle θs with time, FIG. 4D shows the variation of the counter value of a counter C (Tk) with time, and FIG. 4E shows the variation of the voltage representing the air-fuel ratio detected by the downstream $O_2$ sensor with time;

FIGS. 5A and 5B are diagrams showing data acquired while the vehicle equipped with the failure diagnostic apparatus for the air-fuel ratio detecting device shown in FIG. 1 is running after warm-up, wherein FIG. 5A shows the variation of the vehicle speed with time and FIG. 5B shows the variation of the voltage representing the air-fuel ratio detected by the downstream $O_2$ sensor with time;

FIGS. 11A–11C are waveform charts showing the functions of a known failure diagnostic apparatus for an air-fuel ratio detecting device, wherein FIG. 11A shows whether a fuel cut operation is carried out or not, FIG. 11B shows the variation of the voltage representing the air-fuel ratio detected by an upstream $O_2$ sensor with time, and FIG. 11C shows the variation of the voltage representing the air-fuel ratio detected by a downstream $O_2$ sensor with time;

DETAILED DESCRIPTION OF THE INVENTION

The present invention will now be described in detail with reference to the drawings showing a preferred embodiment thereof.

A failure diagnostic apparatus for air fuel ratio detecting means according to the present invention is annexed to an engine controller 2 serving as control means for controlling an engine 1 of a vehicle, not shown. The engine controller 2 constitutes a control function section of the failure diagnostic apparatus for the air-fuel ratio detecting means.

Figure 1:
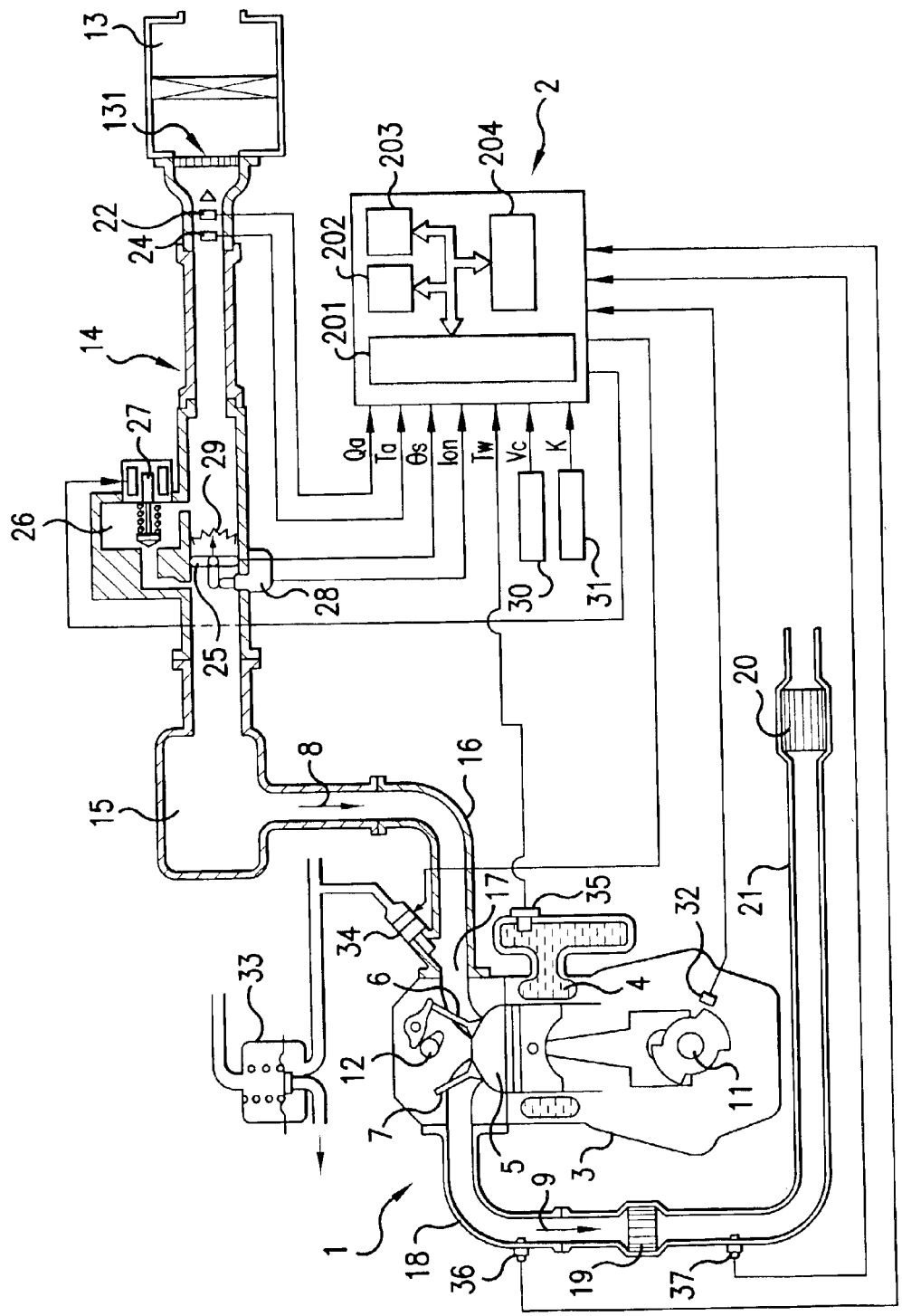
FIG. 1 is a schematic diagram showing the construction of an engine of a vehicle to which is applied a failure diagnostic apparatus for an air-fuel ratio detecting device according to an embodiment of the present invention.

The engine 1 shown in FIG. 1 is a multiple cylinder engine, and a plurality of cylinders are serially disposed in a direction vertical to the paper surface of FIG. 1 in a body 3 of the engine 1. The plurality of cylinders are surrounded by a water jacket 4 of a cooling circuit. A combustion chamber 5 for the cylinders is capable of coming into communication with an intake passage 8 and an exhaust passage 9 via an intake valve 6 and an exhaust valve 7. The intake valve 6 and the exhaust valve 7 are actuated by a valve driving system, not shown, having an intake cam shaft 12 moving in response to the movement of an engine crank shaft 11.

The intake passage 8 is comprised of an air cleaner 13, an intake pipe 14, a surge tank 15, an intake manifold 16, and an intake port 17. The air that passes through the air cleaner 13 flows into the intake passage 8 via the intake pipe 14, the surge tank 15, the intake manifold 16, and the intake port 17 in this order, and flows into the combustion chamber 5 when the intake valve 6 is opened.

An air flow sensor 22 that detects and outputs an intake air volume Qa is disposed in the vicinity of an outlet 9 port 131 of the air cleaner 13, and an intake air temperature sensor 24 that detects and outputs an intake air temperature Ta is disposed downstream of and in the vicinity of the air flow sensor 22. The detected intake air volume Qa and intake air temperature Ta are outputted to the engine controller 2.

A throttle valve 25 and a bypass passage 26 that bypasses the throttle valve 25 are arranged in parallel between the air cleaner 13 and the surge tank 15 in the intake passage 8. An idle speed control valve 27 that is opened or closed to connect or disconnect the intake passage 8 and the bypass passage 26 and control the intake air volume during idling to control the idle speed is disposed in the bypass passage 26. An idle switch 28, which is turned on in response to the full closure of the throttle valve 25, and a throttle sensor 29, which detects the angle θs of the throttle valve 25, are disposed in the vicinity of the throttle valve 25.

The exhaust passage 9 is comprised of an exhaust port, an exhaust manifold 18, and an exhaust pipe 21. The exhaust gas, which is emitted from the combustion chamber 5 when the exhaust valve 7 is opened, flows in the exhaust passage 9 via the exhaust port, the exhaust manifold 18, and the exhaust pipe 21 in this order, and is emitted into the atmosphere through a muffler, not shown. In the exhaust pipe 21, an upstream catalyst 19, which has a relatively small capacity and is capable of activating quickly, is provided at the upstream side, and a downstream catalyst 20, which has a relatively large capacity and is capable of purifying exhaust with an excellent durability, is provided at the downstream side. The upstream catalyst 19 and the downstream catalyst 20 are three-way catalysts serving as exhaust emission purifying device, and are capable of oxidizing HC and CO in exhaust gases and reducing $NO_x$ to purify exhaust emission.

In the vicinity of the upstream catalyst 19, an upstream $O_2$ sensor 36 and a downstream $O_2$ sensor 37, serving as air-fuel ratio detecting device for detecting the air-fuel ratio of exhaust in the exhaust passage 9, are provided at the upstream side and the downstream side, respectively. The air-fuel ratio VO2F outputted from the upstream $O_2$ sensor 36 and the air-fuel ratio VO2R outputted from the downstream $O_2$ sensor 37 are outputted to the engine controller 2. It should be noted that the upstream $O_2$ sensor 36 and the downstream $O_2$ sensor 37 output the voltage within the range of 0 to 1.0 V as the air-fuel ratios VO2F and VO2R, and the voltage is lower if the air-fuel ratio is lean and is higher if the air-fuel ratio is rich.

Further, a vehicle speed signal Vc outputted from a vehicle speed sensor 30, a key-on signal K outputted from a key sensor 31 when an engine key is turned on, a unit crank angle signal dθ (engine speed signal Ne) outputted from a crank angle sensor 32 when the engine 1 is rotating, and a cooling water temperature Tw of cooling water in the water jacket 4 outputted from an engine cooling water temperature sensor 35 are inputted to the engine controller 2.

An injector (fuel injection valve) 34, which injects fuel toward the intake port 17, is provided in the vicinity of the downstream end of the intake manifold 16. The injector 34 is supplied with fuel that has been pressure-regulated by a pressure regulating means 33 disposed in a fuel supply passage, and injects the pressurized fuel in response to an injection signal Tinj transmitted from the engine controller 2.

The engine controller 2 is comprised of an input/output interface 201, a storage section 202, a nonvolatile memory 203 for battery backup, and a central processing section 204. The engine controller 2 is capable of providing fuel control, ignition timing control, and intake air control for the engine 1, and is also capable of determining whether the downstream $O_2$ sensor 37, as the air-fuel ratio detecting device, has failed or not.

Incidentally, as shown in FIG. 2, the engine controller 2 is comprised of a first determination unit A1, a second determination unit A2, an arithmetic operation unit A3, and a failure diagnosis unit A4, which constitute a failure diagnostic function section of the downstream $O_2$ sensor 37.

The first determination unit A1 determines whether the engine 1 has been operated in a first operating state, in which the air-fuel ratio of exhaust in the vicinity of the upstream catalyst 19 and more particularly, exhaust in the vicinity of the downstream $O_2$ sensor 37 is estimated to be rich (refer to FIG. 3D), for a longer period of time than a first predetermined period of time tα1 (such as about 10 seconds) or not. In the first operating state, the air-fuel ratio VO2R, detected by the downstream $O_2$ sensor 37, is equal to or greater than 0.45 V. The first determination unit A1 also determines whether a total period of time ΣTt in which the engine 1 has been operated in the first operating state has exceeded the first predetermined period of time tα1 or not.

The second determination unit A2 determines whether the engine 1 has been operated in a second operating state, in which the air-fuel ratio of exhaust in the vicinity of the upstream catalyst 19 and more particularly, exhaust in the vicinity of the downstream $O_2$ sensor 37 is estimated be lean (refer to FIG. 4D), for a longer period of time than a second predetermined period of time tα2 (such as about 2 seconds). In the second operating state, the air-fuel ratio VO2R, detected by the downstream $O_2$ sensor 37, is less than 0.45 V. The second determination unit A2 also determines whether a period of time (duration) ΣTt in which the engine 1 has been continuously operated in the second operating state has exceeded the second predetermined period of time tα2 or not.

If the first determination unit A1 determines that the engine 1 has been operated in the first operating state for a longer period of time than the first predetermined period of time tα1 and the second determination unit A2 determines that the engine 1 has been operated in the second operating state for a longer period of time than the second predetermined period of time tα2, the arithmetic operation unit A3 calculates the difference ΔVO2R (=VO2Rmax−VO2Rmin) between the maximum output value (the richest air-fuel ratio) and the minimum output value (the leanest air-fuel ratio) of the air-fuel ratios VO2R detected by the downstream $O_2$ sensor 37.

The failure diagnosis unit A4 determines that the downstream $O_2$ sensor 37 has failed if the difference ΔVO2R (refer to FIG. 5B) found by the arithmetic operation means A3 is less than a predetermined value ΔVO2Rα.

A description will now be given of the first operating state and the total period of time ΣTt in which the engine 1 is operated in the first operating state.

The state in which the engine speed Ne is greater than 1500 rpm, the cylinder charging efficiency Ev as engine load is greater than 40%, and the vehicle speed Vc is greater than 30 km/h after the completion of warm-up at a water temperature of 76° C. or greater is set as the first operating state in which the air-fuel ratio of exhaust in the vicinity of the downstream $O_2$ sensor 37 is estimated to be rich to such an extent that the air-fuel ratio VO2R is equal to or greater than 0.45 V. The first operating state assumes that the vehicle has started accelerating from a standstill at the time point t1 as shown in FIGS. 3A to 3E and is operating at a rich air-fuel ratio.

The total period of time ΣTt, in which the engine 1 is operated in the first operating state, is measured by the counter C (ΣTt). As shown in FIG. 3D, for example, the counter C (ΣTt) is set (started) when the engine 1 starts operating in the first operating state at a time point t2, and is stopped when the engine 1 stops operating in the first operating state at a time point t3. In this example, every time the engine 1 starts operating in the first operating state (time points t2 and t4), a counter value of the counter C (ΣTt) is added to the total period of time ΣTt, and data on the air-fuel ratio VO2R outputted in the first operating state is captured until the total period of time ΣTt exceeds the first predetermined period of time tα1 (such as about 10 seconds), so that data including the maximum output value (VO2Rmax) is stored.

The first predetermined period of time tα1 is determined on the assumption that the data is captured and noises are removed. More specifically, an optimum value is selected as the first predetermined period of time tα1, considering that the frequency of failure detecting processing is lowered if the first predetermined period of time tα1 is too long. The first predetermined period of time tα1 is not limited to 10 seconds.

In this manner, it is determined whether the engine 1 has been operated in the first operating state for a longer time than the first predetermined period of time tα1, and the total period of time ΣTt in which the engine 1 is operated in the first operating state is measured. Thus, if, after the engine 1 is brought into the first operating state, the vehicle continues running with the vehicle speed intermittently becoming lower than 30 km/h, time periods Δtm and Δtn, in which the engine 1 is operated in the first operating state, are sequentially added. The data on the air-fuel ratios VO2R is until the total period of time ΣTt, in which the engine 1 has been operated in the first operating state, exceeds the first predetermined period of time tα1 (such as about 10 seconds), so that data including the maximum output value (VO2Rmax) is stored.

A description will now be given of the second operating state and the duration Tk the second operating state continues.

In this example, the fuel cut state or the intake air volume cut state after warm-up at a water temperature Tw of 76° C. or higher is set as the second operating state in which the air-fuel ratio of exhaust gas in the vicinity of the downstream $O_2$ sensor 37 is estimated to be lean to such an extent that the air-fuel ratio VO2R is less than 0.45 V. The second operating state assumes that the throttle angle θs reaches the full closure angle (refer to FIG. 4C) in order to decelerate the running vehicle and the engine 1 is operating at a lean air-fuel ratio because no fuel is injected in the fuel cut operation as shown in FIGS. 4A to 4E.

The duration Tk of the second operating state is measured by counting with a counter C (Tk), and whether the second operating state has continued for a longer period of time than a second predetermined period of time tα2 (2 seconds) or not is determined according to the counter value of the counter C (Tk). As shown in FIG. 4D, the counter C (Tk) is set (started) when the engine 1 starts operating in the second operating state at a time point t6, and is stopped and reset (cr) when the counter value of the counter C (Tk) exceeds a predetermined value, i.e. when the period of time Tk exceeds the second predetermined period of time tα2 at a time point t7. While the engine 1 is operated in the second operating state, data on the detected air-fuel ratios VO2R is captured.

The second predetermined period of time tα2 is set to about 2 seconds in which, after the throttle angle θs reaches the full closure angle to bring the engine 1 into the fuel cut state, the air-fuel ratio VO2R rapidly lowers because no fuel is injected and surely varies to such an extent that it can be determined that the air-fuel ratio VO2R has clearly changed from the air-fuel ratio VO2R detected before the engine 1 starts operating in the fuel cut state. The second predetermined period of time tα2, however, is not limited to 2 seconds insofar as an optimum value is selected considering that a sufficient drop in the air-fuel ratio VO2R cannot be detected if the second predetermined period of time tα2 is too short, and the frequency of failure detecting processing is lowered if the second predetermined period of time tα2 is too long.

A description will now be given of a predetermined value ΔVO2Rα used by the failure diagnosis unit A4.

The predetermined value ΔVO2Rα must be set to such a value as to determine whether or not the downstream $O_2$ sensor 37 has failed or deteriorated, and in this example, the predetermined value ΔVO2Rα is set to 0.3 V. Whether or not the downstream $O_2$ sensor 37 has failed due to malfunction caused by sticking or deterioration is determined by using the predetermined value ΔVO2Rα. Whether or not the downstream $O_2$ sensor 37 has failed due to sticking is determined without determining whether the $O_2$ sensor 37 has failed or not may be determined by adopting a value of 0.3 V or less as the predetermined value ΔVO2Rα.

In a failure diagnosing process carried out by the air-fuel ratio detecting device in this example, the number of times D/C the difference ΔVO2R is determined as being less than the predetermined value ΔVO2Rα (0.3 V) is sequentially counted by a failure determination frequency counter C (D/C). If the number of times D/C is detected repeatedly three times, it is then determined that the downstream $O_2$ sensor 37 has failed, so that noises are removed to ensure the reliability of data. It should not necessarily be determined that the downstream $O_2$ sensor 37 has failed only if the number of times D/C is detected a plurality of times, but it may be determined that the downstream $O_2$ sensor 37 has failed if it is determined only once that the difference ΔVO2R is less than the predetermined value ΔVO2Rα.

Figure 6:
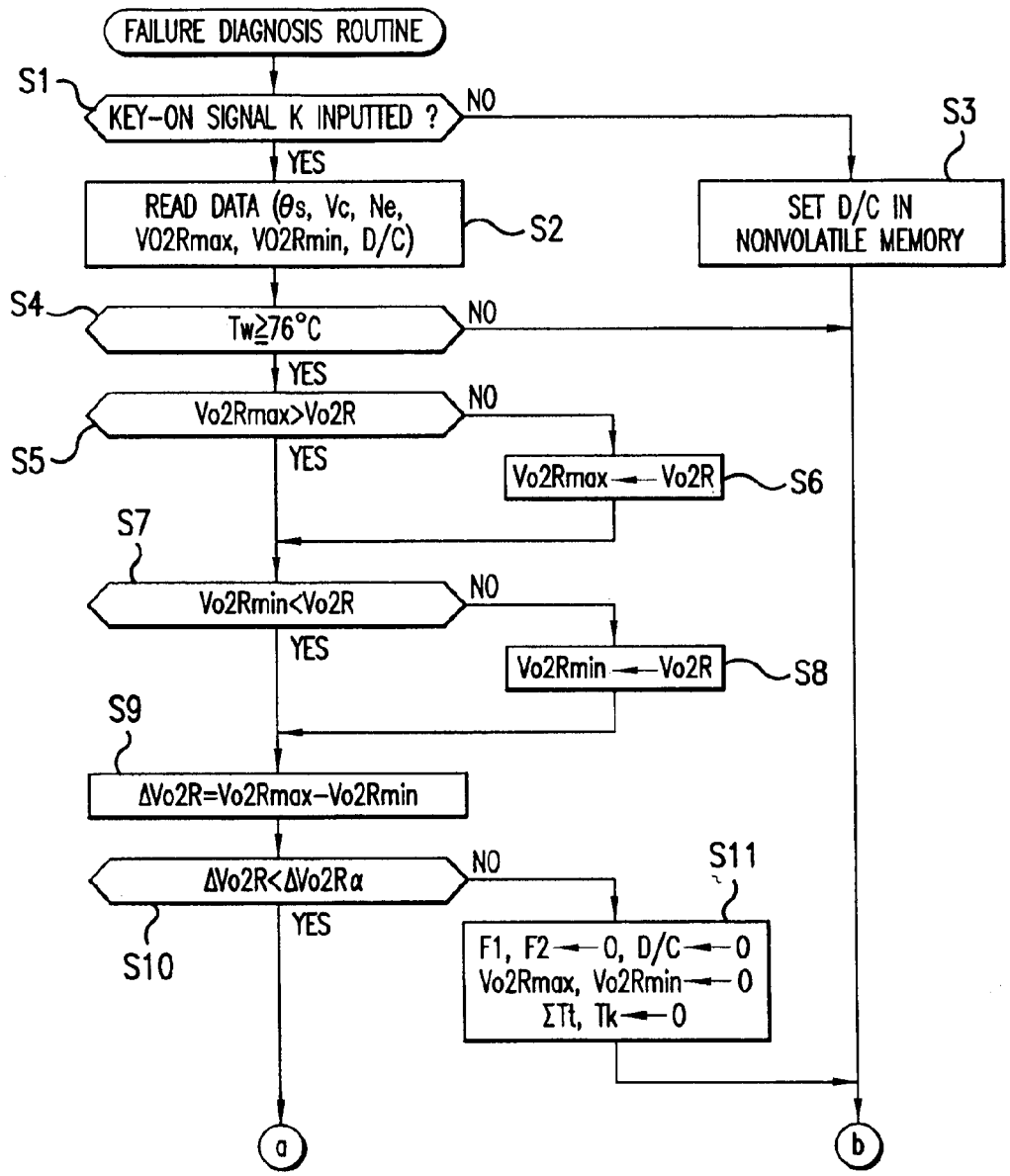
FIG. 6 is a flow chart showing a failure diagnosis routine executed by an engine controller shown in FIG. 1.
Figure 7:
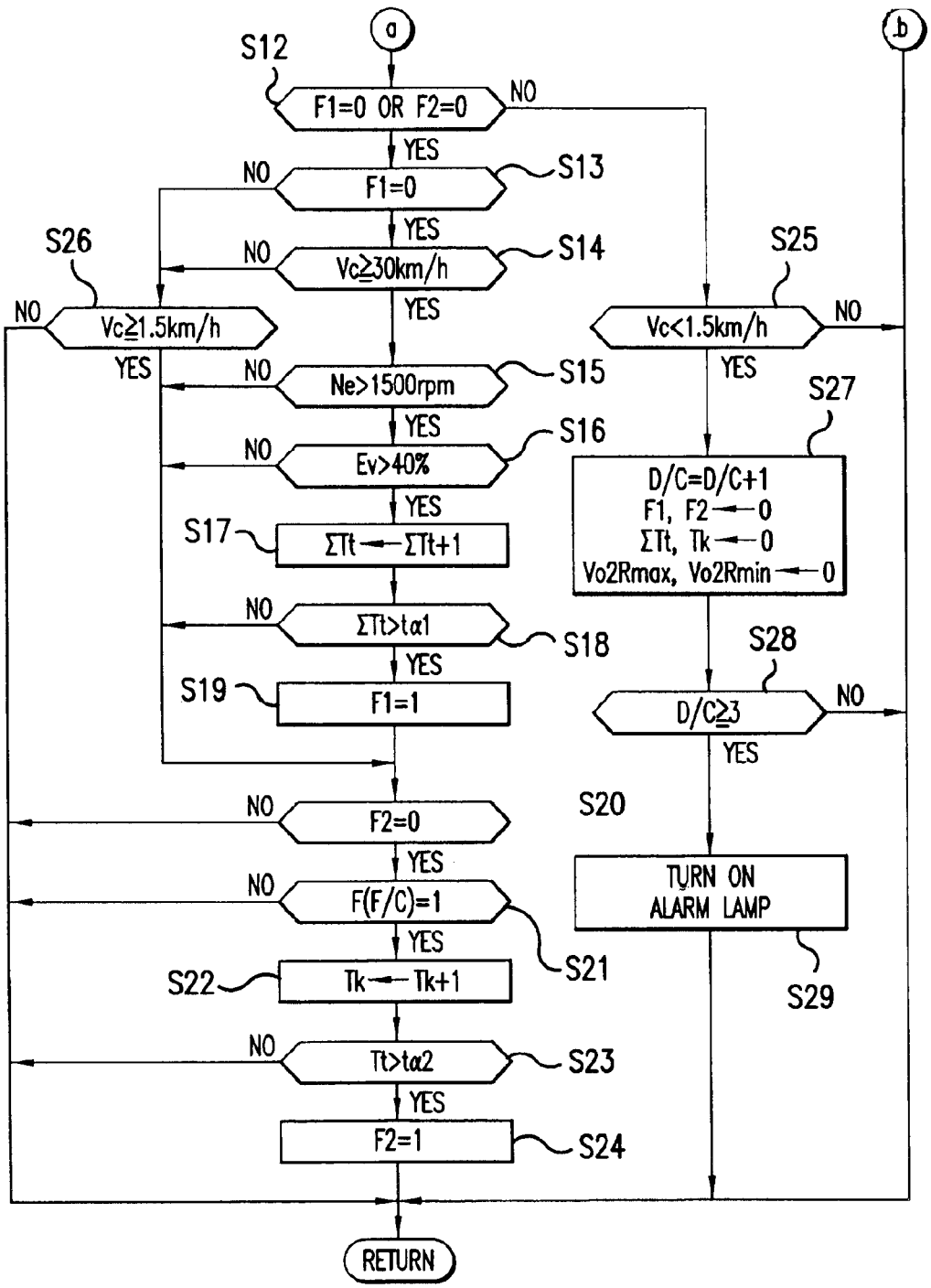
FIG. 7 is a flow chart showing a continued part of the failure diagnosis routine of FIG. 6.
Figure 8:
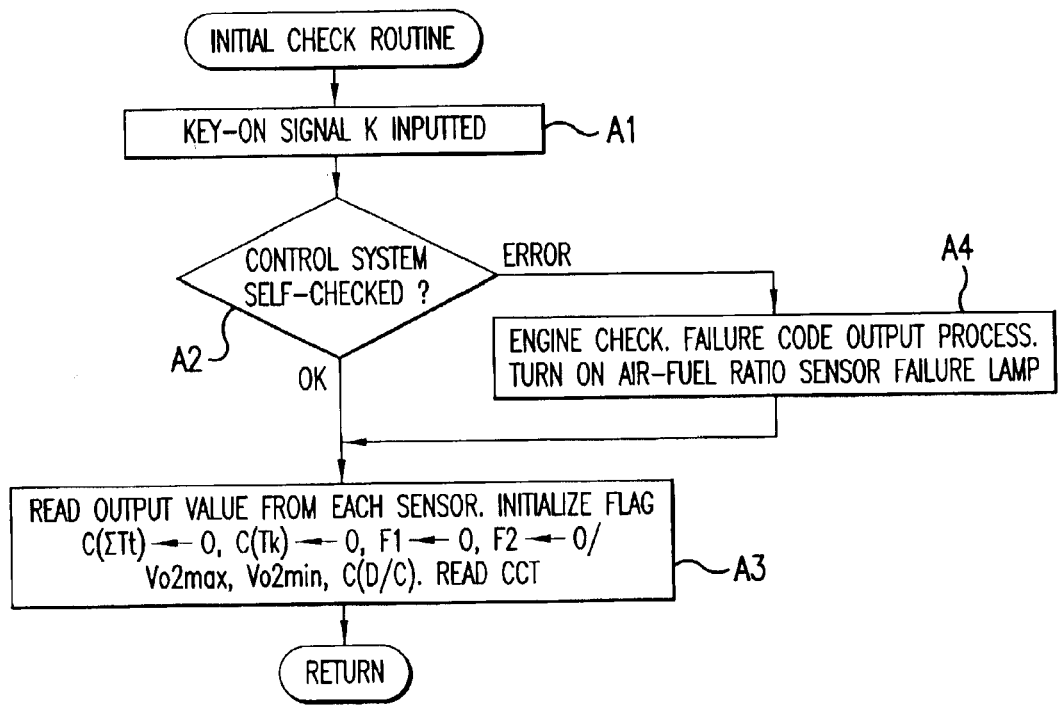
FIG. 8 is a flow chart showing an initial check routine executed by the engine controller shown in FIG. 1.

A description will now be given of the failure diagnosing process carried out by the air-fuel ratio detecting device shown in FIG. 1 with reference to FIGS. 3 to 10. FIGS. 3 and 4 are views showing a failure diagnosing function of the air-fuel ratio detecting device, FIGS. 5A and 5B are waveform charts showing the relation between the vehicle speed and the air-fuel ratio VO2R, FIGS. 6 and 7 are flow charts showing the failure diagnosing process carried out by the air-fuel ratio detecting device, and FIGS. 8 to 10 are flow charts showing an initial check routine, an air-fuel ratio control routine, and an injector driving routine, respectively.

When the vehicle, not shown, equipped with a failure diagnostic device for the air-fuel ratio detecting device is started, the engine controller 2 starts an initial checking process of a main routine, not shown, in response to the engine key-on signal K transmitted from the key sensor 31. As shown in FIG. 8, in the initial check routine, it is determined in Step A1 whether the key-on signal K has been inputted or not, and in Step A2, it is self-checked whether devices and sensors related to a plurality of functions of the engine controller 2, such as intake control function, fuel control function, and ignition control function, are normal or not, and it is also determined whether the result obtained by he failure diagnosing process carried out by the air-fuel ratio detecting device is normal or not. If it is determined to be normal, the process proceeds to Step A3, and if determined to be abnormal, the process proceeds to Step A4. In Step A4, a code related to the abnormal control function is outputted and a failure lamp of each failure sensor such as the downstream $O_2$ sensor 37 is turned on, and the process proceeds to Step A3.

In Step A3, the values outputted by the sensors related to the intake control, fuel control, ignition timing control, and the like, i.e., the intake air temperature Ta detected by the intake air temperature sensor 24, the intake air volume Qa detected by the air flow sensor 22, the angle θs of the throttle valve 25 detected by the throttle sensor 29, a turning-on signal Ion transmitted from the idle switch 28, the water temperature Tw detected by the water temperature sensor 35, the key-on signal K transmitted from the key sensor 31, the engine speed signal Ne transmitted from the crank angle sensor 32, the air-fuel ratio VO2F detected by the upstream $O_2$ sensor 36, the air-fuel ratio Vo2R detected by the downstream $O_2$ sensor 37, and so forth are read. Further, the counter C (ΣTt) and C(Tk) are reset, a variety of flags such as a first flag F1 and a second flag F2, described later, are cleared, and the number of times counted by the failure determination frequency counter (D/C) and stored in operations up to the present is read from the nonvolatile memory 203, and the process returns to the main routine, not shown.

Figure 9:
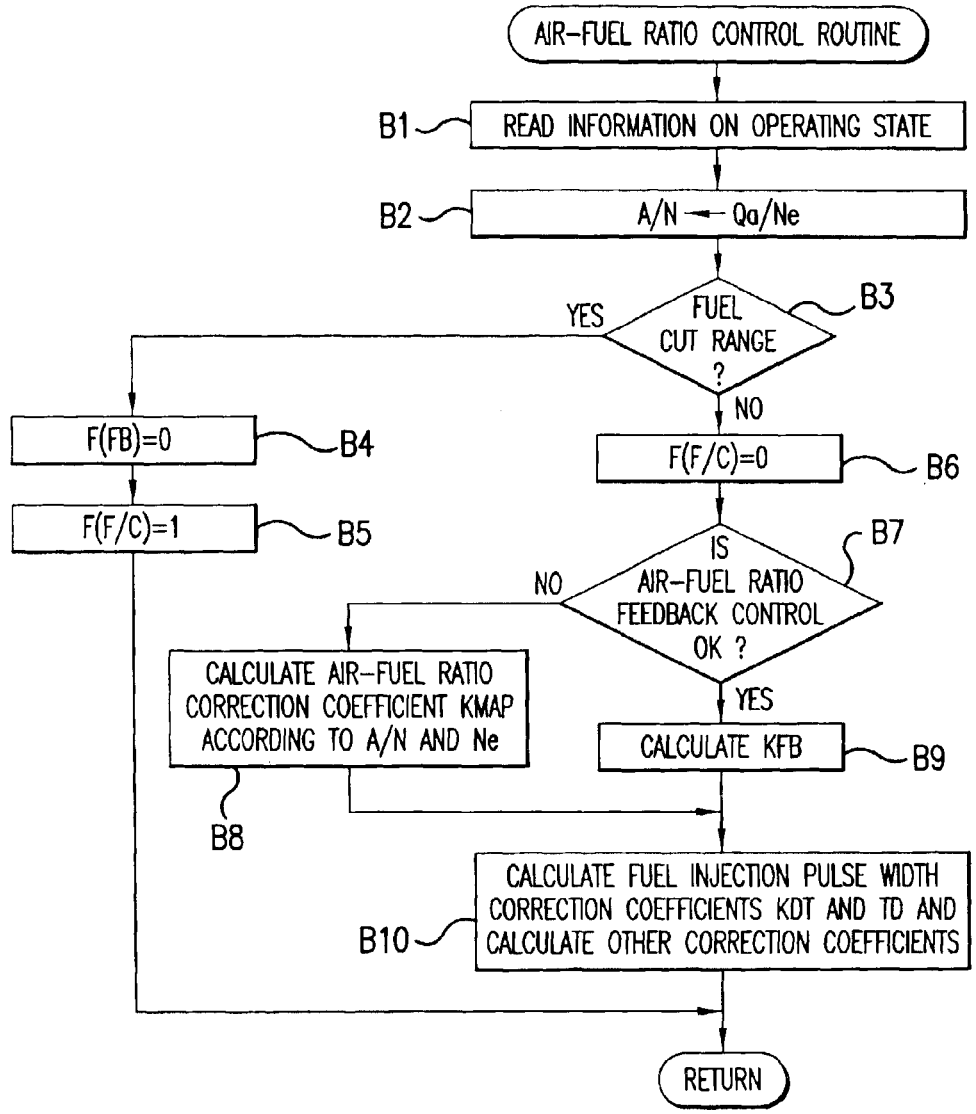
FIG. 9 is a flow chart showing an air-fuel ratio control routine executed by the engine controller shown in FIG. 1.
Figure 10:
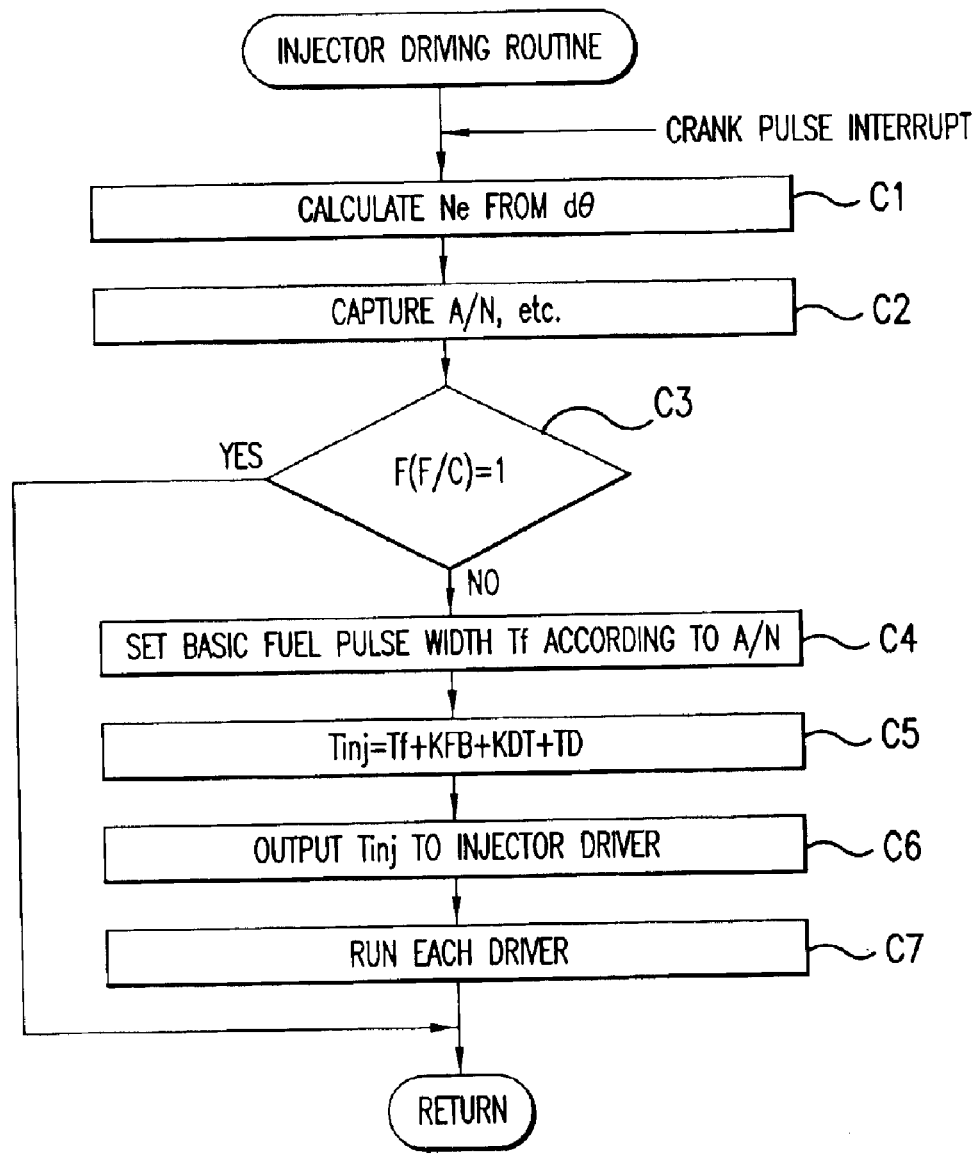
FIG. 10 is a flow chart showing an injector driving routine executed by the engine controller shown in FIG. 1.

In the course of the main routine, the engine controller 2 starts the air-fuel ratio control routine shown in FIG. 9 and the injector driving routine shown in FIG. 10.

In the air-fuel ratio control routine, operational information such as the intake air volume Qa, the engine speed Ne, the throttle angle θs, the water temperature Tw, the air-fuel ratios VO2F and VO2R, the intake air temperature Ta, and so forth are captured in Step B1.

As shown in FIG. 9, in Step B2, the intake air volume Qa is divided by the engine speed Ne to calculate the intake air volume A/N per stroke. In Step B3, whether the operation range of the engine 1 lies in the fuel cut range or not is determined using an operational range map, not shown. If the operation range lies in the fuel cut range as described with reference to FIGS. 4A to 4E, an air-fuel ratio feedback flag F (FB) is cleared in Step B4, and a fuel cut flag F (F/C) is set to 1 in Step B5. The process then returns to the main routine.

On the other hand, if it is determine in Step B3 that the operation range does not lie in the fuel cut range, the fuel cut flag F (F/C) is reset in Step B6, and it is determined in Step B7 whether he air-fuel ratio feedback conditions are satisfied or not. If the operation range of the engine 1 lies in a transitional operation range as in the case of accelerating as described with reference to FIGS. 3A to 3E and if the water temperature Tw is equal to or less than a predetermined value, it is determined that the air-fuel ratio feedback conditions are not satisfied, and in Step B8, the air fuel ratio correction coefficient KMAP is calculated according to the present operational information (A/N and Ne) The process then proceeds to Step B10.

Figures 11A, 11B, 11C:
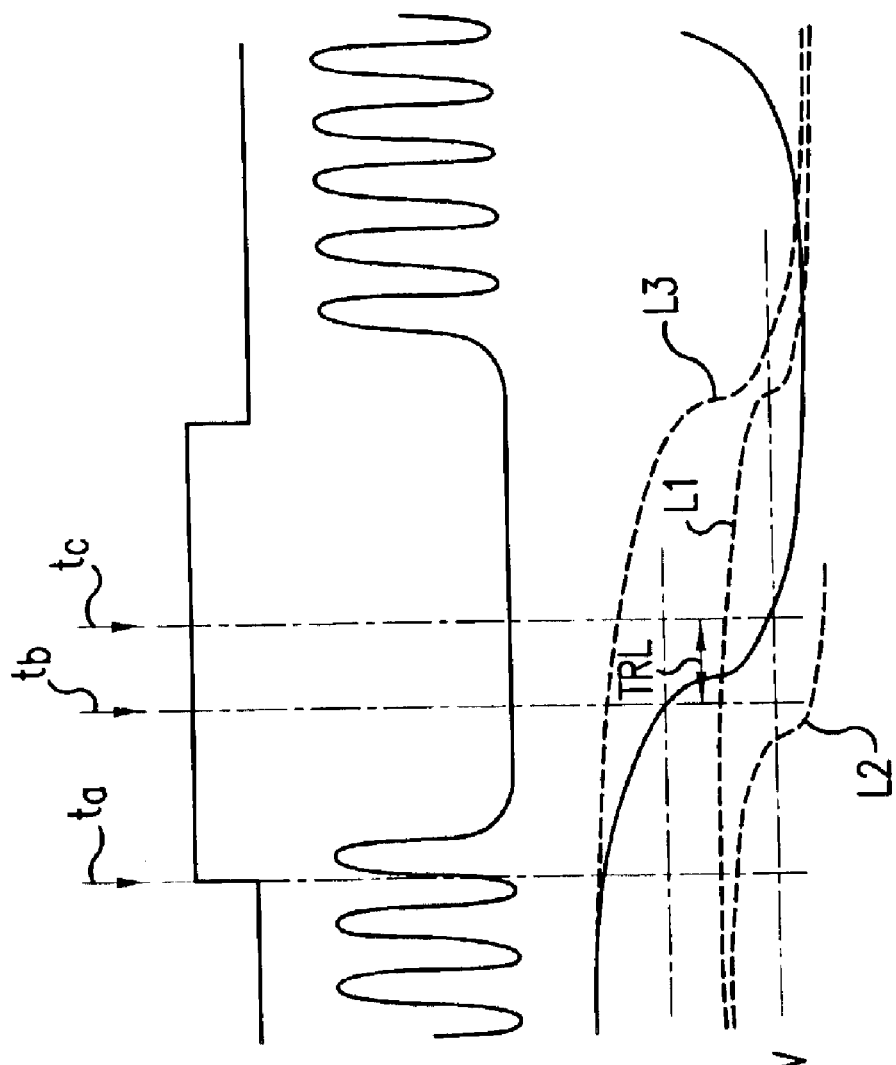

If it is determined in Step B7 hat the air-fuel ratio feedback conditions are satisfied, the fuel volume correction coefficient KFB is calculated based on the air-fuel ratio VO2F detected by the upstream $O_2$ sensor 36 in Step B9. Incidentally, if the air-fuel ratio feedback conditions are satisfied to bring the engine 1 into the stoichiometric air-fuel ratio operation range, the air-fuel ratio correction coefficient KFB is corrected and outputted so that it can be ascertained that the actual air-fuel ratio is alternately switched between a rich air-fuel ratio and a lean air-fuel ratio within a predetermined width about a stoichiometric air-fuel ratio (refer to FIG. 11B. It should be noted that the air-fuel ratio correction coefficient KMAP and the fuel volume correction coefficient KFB are calculated in a manner disclosed in Japanese Laid-Open Patent Publication (Kokai) No. 64-53043 or the like.

In Step B10, the fuel injection pulse width correction coefficient KDT and the fuel injection valve dead time correction value TD are calculated according to the operating conditions, and the process returns to the main routine.

In the course of the main routine, the injector driving routine shown in FIG. 10 is started in response to the input of a crank pulse for discriminating the cylinders. First, in Step C1, the engine speed Ne is calculated from the unit crank angle signal dθ transmitted from the crank angle sensor 32, and in Step C2, the intake air volume A/N, fuel volume correction coefficient KFB, fuel injection pulse width correction coefficient KDT, and fuel injection valve dead time correction value TD found in Steps B2, B9, and B11 are captured. The process then proceeds to Step C3 wherein it is determined whether the engine 1 is being operated in the fuel cut state described with reference to FIGS. 4A to 4E, in other words, whether the operation range of the engine 1 lies in the fuel cut range or not. In this example, whether the fuel cut flag F (F/C) is 1 or 0 is determined. If the fuel cut flag F (F/C) is 1, that is, if the engine 1 is being operated in the fuel cut state, the process returns to the start of the injector driving routine without injecting fuel. If the fuel cut flag F (F/C) is 0, the process proceeds to Step C4 wherein the basic fuel injection pulse width Tf corresponding to the intake air volume A/N is set, and in Step C5, the fuel injection pulse width Tinj (=tf×FB× KDT+TD) is calculated. On this occasion, if the vehicle is accelerating as described with reference to FIGS. 3A to 3E, the basic fuel injection pulse width Tf is corrected to be increased, enabling the engine 1 to operate at a rich air-fuel ratio.

In Step C6, the fuel injection pulse width Tinj is outputted to each injector driver, and in Step C7, each driver is run. The process then returns to the main routine. As a result, each injector 34 injects fuel according to the fuel injection pulse width Tinj.

Further, in the process of the main routine, whether the air-fuel ratio detecting device has failed or not is determined as needed as shown in FIGS. 6 and 7.

As shown in FIG. 6, to determine whether the air-fuel ratio detecting device has failed or not, it is ascertained in Step S1 whether the key-on signal K has been inputted or not from the key sensor 31. If the key-on signal K has been inputted, the process proceeds to Step S2, and if the key-on signal K has not been inputted, the process proceeds to Step S3. In Step S2, the newest throttle valve angle θs, vehicle speed Vc, engine speed Ne, and cylinder charging efficiency Ev, the maximum output value (the richest air-fuel ratio) VO2Rmax and the minimum output value (the leanest air-fuel ratio) VO2Rmin outputted from the downstream $O_2$ sensor, which are stored in the storage section 202 of the engine controller 2, and the number of times D/C counted by the failure determination frequency counter C (D/C), which is stored in the nonvolatile memory 203, and so forth are read to be used in the failure diagnosis routine, and the process then proceeds to Step S4.

In Step S4, it is determined whether the present water temperature Tw is greater than a warm-up completion value (such as about 76° C.) or not. If it is determined that the present water temperature Tw is greater than the warm-up completion value, the process proceeds to Step S5, and if it is determined whether the present water temperature Tw is less than the warm-up completion value, the process returns to the main routine to wait for the warm-up to be completed.

In Step S5, it is determined whether the maximum output value VO2Rmax, stored in the storage section 202 at the present moment, is greater than the newest air-fuel ratio VO2R detected by the downstream $O_2$ sensor 37 or not. If the newest air-fuel ratio VO2R is greater than the present maximum output value VO2Rmax, the process proceeds to Step S6 wherein the maximum output value VO2Rmax is updated to the newest air-fuel ratio VO2R, and the process then proceeds to Step S7. In Step S7, it is determined whether the minimum output value VO2Rmin stored in the storage section 202 at the present moment is less than the newest air-fuel ratio VO2R detected by the downstream $O_2$ sensor 37 or not. If the newest air-fuel ratio VO2R is less than the present minimum output value VO2Rmin, the process proceeds to Step S6 wherein the minimum output value VO2Rmin is updated to the newest air-fuel ratio VO2R, and the process then proceeds to Step S9. It should be noted that, if the maximum output value VO2Rmax or the minimum output value VO2Rmin is updated in Step S6 or S8, the updated maximum output value VO2Rmax or minimum output value VO2Rmin is stored in the storage section 202.

If the process proceeds to Step S9 after Steps S7 and S8, the difference between the maximum output value VO2Rmax and the minimum output value VO2Rmin is calculated as the variation $\Delta$VO2R (=VO2Rmax−VO2Rmin), and the process then proceeds to Step S10.

In Step S10, it is determined whether the variation $\Delta$VO2R is less than a failure determination predetermined value $\Delta$VO2R (e.g., 0.3 V) or not. If it is determined that the variation $\Delta$VO2R is equal to or greater than the predetermined value $\Delta$VO2R$\alpha$ and the air-fuel ratio VO2R has varied to a sufficient degree, the process proceeds to Step S11, and if the variation $\Delta$VO2R is less than the predetermined value $\Delta$VO2R$\alpha$, the process proceeds to Step S12.

In the case where it is determined, in Step S10, that the variation $\Delta$VO2R is sufficient, for example, the case where a time point te in FIG. 5 is reached indicates that a case where it can be ascertained that the variation $\Delta$VO2R in the air-fuel ratio detected by the downstream O$_2$ sensor 37 up to the present is equal to or greater than the predetermined value $\Delta$VO2R$\alpha$ and the downstream O$_2$ sensor 37 is normally operating. In this case, the process proceeds to Step S11 wherein the present failure diagnosis result is cleared, in other words, the present first flag F1 and second flag F2, the counter value D/C of the failure determination frequency counter C (D/C), the maximum output value VO2Rmax and the minimum output value VO2Rmin, and the counter values $\Sigma$Tt and Tk of the counters C ($\Sigma$Tt) and C(Tk), described later, are reset, and the process returns to the main routine.

On the other hand, if the variation $\Delta$VO2R is less than the predetermined value $\Delta$VO2R$\alpha$ due to deterioration of the downstream O$_2$ sensor 37 or the like, the air-fuel ratio VO2R varies as indicated by a two-dot chain line shown in FIG. 5B, for example, and if the variation $\Delta$VO2R is equal to a variation $\Delta$VO2R', the process proceeds to Step S12.

In Step S12, it is determined whether at least one of the first flag F1 and the second flag F2 is 0 or not. The first flag F1 is set to 1 in the case where the first determination unit A1 determines that the engine 1 has been operated in the first operating state, in which the air-fuel ratio of exhaust in the vicinity of the upstream catalyst 19, and more particularly, the air-fuel ratio of exhaust in the vicinity of the downstream O$_2$ sensor 37 is estimated to be rich, for a longer period of time than the first predetermined period of time t$\alpha$1 (such as about 10 seconds). The second flag F2 is set to 1 in the case where the second determination unit A2 determines that the engine 1 has been operated in the second operating state, in which the air-fuel ratio of exhaust in the vicinity of the upstream catalyst 19, and more particularly, the air-fuel ratio of exhaust in the vicinity of the downstream O$_2$ sensor 37 is estimated to be lean, for a longer period of time than the second predetermined period of time t$\alpha$2 (such as about 2 seconds).

If at least one of the first flag F1 an the second flag F2 is 0, for example, if both the first flag F1 and the second flag F2 are 0 just after the start of the engine 1, the process proceeds to Step S13 wherein it is determined whether the first flag F1 is 0 or not. If the first determination unit A1 does not determine that the engine 1 has been operated in the first operating state for a longer period of time than the first predetermined period of time t$\alpha$1 (such as about 10 seconds) and the first flag F1 is set to 0, the process proceeds to Step S14 wherein it is determined whether or not the vehicle speed Vc is equal to or greater than a predetermined vehicle speed (such as about 30 km/h) For example, if the vehicle speed Vc becomes equal to or greater than about 30 km/h at the time point t2 in FIG. 3A, the process proceeds to Steps S15 and S16.

In Step S15, it is determined whether the engine speed Ne is greater than 1500 rpm or not, and in Step S16, it is determined whether the cylinder charging efficiency Ev is greater than 40% or not. If the vehicle speed is equal to or greater than 30 km/h, the engine speed Ne is greater than 1500 rpm, and the cylinder charging efficiency Ev is greater than 40%, it is then determined that the engine 1 is being operated in the first operating state based on the estimation that the air-fuel ratio of exhaust in the vicinity of the downstream O$_2$ sensor 37 is rich, and the process proceeds to Step S17. In Step S17, the counter value $\Sigma$Tt. of the counter C ($\Sigma$Tt) is incremented by 1 to measure a period of time in which the engine 1 is operated in the first operating state. If it is determined that the engine 1 starts operating in the first operating state at the time points t2 and t4, for example, the counter C ($\Sigma$Tt) is started, and a period of time, in which the engine 1 is operated in the first operating state, is measured and represented as the counter value $\Sigma$Tt by the counter C ($\Sigma$Tt).

If it is determined that the engine 1 is not being operated in the first operating state, for example, at the time point t3 shown in FIG. 3A, the counter C ($\Sigma$Tt) does not clear but holds the counter value $\Sigma$Tt represented at present as shown in FIG. 3D, and thereafter, if it is then determined that the engine 1 is being operated in the first operating state, for example, at the time point t4 shown in FIG. 3A, the counter C ($\Sigma$Tt) starts counting from the held counter value $\Sigma$Tt. Therefore, the counter C ($\Sigma$Tt) measures the total period of time in which the engine 1 is operated in the first operating state.

In Step S18, it is determined whether the counter value $\Sigma$Tt of the counter C ($\Sigma$Tt), i.e., the total period of time in which the engine 1 is operated in the first operating state has exceeded the first predetermined period of time t$\alpha$1 (such as about 10 seconds) or not. If it is determined that the counter value $\Sigma$Tt of the counter C ($\Sigma$Tt) has exceeded the first predetermined period of time t$\alpha$1, the first flag F1 is set to 1 in Step S19, and the process then proceeds to Step S20.

If it is determined in Step S13 that the first flag F1 is set to 1, and if it is determined in Step S14 that the vehicle speed Vc is less than the predetermined vehicle speed (such as about 30 km/h), the process proceeds to Step S26 wherein it i determined whether or not the vehicle speed Vc is equal to or greater than a standstill vehicle speed (such as about 1.5 km/h). If it is determined that the vehicle speed Vc is less than the standstill vehicle speed, the process returns to the start of the failure diagnosis routine.

If it is determined that the engine 1 is not operated in the first operating state based on the determination in Step S15 that the engine speed Ne is equal to or less than 1500 rpm or the determination in Step S16E that the cylinder charging efficiency Ev is equal to or less than 40%, if it is determined in Step S18 that the counter value $\Sigma$Tt of the counter C ($\Sigma$Tt) is not greater than the first predetermined period of time t$\alpha$1, or if it is determined in Step S26 that the vehicle is not at a standstill, the process proceeds to Step S20.

In Step S20, it is determined whether the second flag F2 is 0 or not. If the second flag F2 is 0, the process proceeds to Step S21 wherein it is determined whether the fuel cut flag F (F/C) set in Steps B3 and B5 of the air-fuel ratio control routine shown in FIG. 9 is 1 or not. If it is determined that the fuel cut flag F (F/C) is 1, i.e. the operation range of the engine 1 lies in the fuel cut operation range, the air-fuel ratio of exhaust in the vicinity of the downstream $O_2$ sensor 37 is estimated to be rich, and if it is determined that the engine 1 is operated in the second operating state, the process proceeds to Step S22 wherein the counter value Tk of the counter C (Tk) is incremented by 1 to measure a period of time in which the engine 1 is operated in the second operating state. If it is determined that the operation range of the engine 1 lies in the fuel cut range and the engine 1 has been brought into the second operating state, for example, at the time point t6 shown in FIGS. 4 and 5, the counter C (Tk) is started, and the period of time in which the engine 1 is operated in the second operating state is measured and represented as the counter value Tk by the counter C (Tk). For example, as shown in FIG. 4D, the counter C (Tk) measures the duration the engine 1 is continuously operated in the second operating state.

In the next Step S23, it is determined whether the counter value Tk of the counter C (Tk), i.e., the duration of the second operating state has exceeded the second predetermined period of time tα2 (such as about 2 seconds) or not. If it is determined that the counter value Tk of the counter C (Tk), i.e., the duration of the second operating state has exceeded the second predetermined period of time tα2, the process proceeds to Step S24 wherein the second flag F2 is set to 1.

Incidentally, if it is determined in Step S20 that the second flag F2 is set to 1, if it is determined in Step S21 that the operation range does not lie in the fuel cut range, and if it is determined in Step S23 that the duration of the second operating state has not exceeded the second predetermined period of time tα2, the process returns to the start of the failure diagnosis routine.

As described above, if it is determined in Steps S13 to S19 that the total period of time in which the engine 1 is operated in the first operating state has exceeded the first predetermined period of time tα1, if it is determined in Steps S20 to S24 that the duration the engine 1 is continuously operated in the second operating state has exceeded the second predetermined period of time tα2, and if the first flag F1 is set to 1 in Step S19 and the second flag F2 is set to 1 in Step S24, it can be determined that the downstream $O_2$ sensor 37 has failed.

If the difference between the maximum output value VO2Rmax and the minimum output value VO2Rmin, stored up to the present time in the storage section 202, i.e., the variation ΔVO2R in the air-fuel ratio VO2R, is less than the predetermined value ΔVO2Rα (0.3 V) even though both the first flag F1 and the second flag F2 are set to 1, in other words, if the engine 1 has been operated in the first operating state for a longer period of time than the first predetermined period of time and has been operated in the second operating state for a longer period of time than the second predetermined period of time, the determination result in Step S12 is negative, and the process proceeds to Step S25. In Step S25, it is determined whether the vehicle speed Vc has become lower than the standstill vehicle speed (such as about 1.5 km/h) or not, waiting for the vehicle to come to a standstill. After checking whether the vehicle has come to a standstill, the next accelerating from standstill can be ascertained, in other words, it can be ascertained that the engine 1 is operated in the first operating state.

If it is determined in Step S25 that the vehicle speed Vc is lower than the standstill vehicle speed and the vehicle is at a standstill, the process proceeds to Step S27 wherein the counter value D/C of the failure determination frequency counter C (D/C) is incremented by 1. Further, the first flag F1 and the second flag F2 are reset, and the counter values of the counter C (ΣTt) and the counter C (Tk) are cleared.

In the next Step S28, it is determined whether or not the counter value D/C of the failure determination frequency counter C (D/C) is equal to or greater than 3, waiting for the counter value D/C to become equal to or greater than 3.

If the transmission of the engine key-on signal K is stopped before the counter value D/C of the failure determination frequency counter C (D/C) becomes equal to or greater than 3, the process proceeds from Step S1 to Step S3 wherein the present counter value D/C of the failure determination frequency counter C (D/C) is stored in the nonvolatile memory 203, and the process is terminated.

On the other hand, if the process repeatedly returns to Step S28 and it is determined in Step S28 that the counter value D/C of the failure determination frequency C CD/c) becomes equal to or greater than 3, it is assumed that there is no diagnosis error due to noises and the downstream $O_2$ sensor 37 has certainly failed, and the process proceeds to Step S29. Specifically, since whether the downstream $O_2$ sensor 37 has failed or not is determined after the failure determination frequency counter C (D/C) performs counting three times, it is possible to carry out accurate failure diagnosis without being affected by noises.

In Step S29, a failure code is outputted and is set in the nonvolatile memory 203, and an alarm lamp, not shown, is turned on. This completes the present control, and the process returns to the main routine. Incidentally, if the process proceeds from Step A2 to Step A4 in the initial check routine executed again, a failure lamp is repeatedly turned on and the failure code set in the nonvolatile memory 203 is displayed on a known multiuse tester connected to a diagnosis connector, not shown, at a suitable time to detect a part in failure and promptly restore it.

In this way, after the completion of warm-up at a water temperature of about 76° C. or higher, the failure diagnostic apparatus for the air-fuel ratio detecting means shown in FIG. 1 calculates the difference between the maximum output value VO2Rmax and the minimum output value VO2Rmin as the variation ΔVO2R in the air-fuel ratio VO2R detected by the downstream $O_2$ sensor 37, measures the total period of time ΣTt in which the engine 1 is operated in the first operating state (Vc>30 km/h, Ne>1500 rpm, and Ev>40%) by the counter C (ΣTt), and measures the duration Tk the engine 1 is continuously operated in the second operating state (the fuel cut operating state) by the counter C (Tk). If it is then determined that the total period of time ΣTt in which the engine 1 is operated in the first operating state is greater than the first predetermined period of time tα1 (such as about 10 seconds), the duration Tk the engine 1 is continuously operated in the second operating state is greater than the second predetermined period of time tα2 (such as about 2 seconds), and the variation ΔVO2R in the air-fuel ratio VO2R detected by the downstream $O_2$ sensor 37 is less than the predetermined value ΔVO2Rα, it is ascertained once that the downstream $O_2$ sensor 37 has failed. Thereafter, if the failure determination frequency counter C (D/C) counts the malfunctioning of the downstream $O_2$ sensor 37 three times, it is then determined that the downstream $O_2$ sensor 37 has failed or deteriorated.

Although in the above described failure diagnosis as to the air-fuel ratio detecting device, if it is determined three times that the total period of time ΣTt in which the engine 1 is operated in the first operating state is greater than the first predetermined period of time tα1 (such as about 10 seconds), the duration Tk the engine 1 is continuously operated in the second operating state is greater than the second predetermined period of time tα2 (such as about 2 seconds), and the variation ΔVO2R in the air-fuel ratio VO2R detected by the downstream O₂ sensor 37 is less than the predetermined value ΔVO2Rα, it is determined that the downstream O₂ sensor 37 has failed, but the number of times of the determination should not be limited to three times. For example, if it is determined only once that the total period of time ΣTt in which the engine 1 is operated in the first operating state is greater than the first predetermined period of time tα1 (such as about 10 seconds), the duration Tk the engine 1 is continuously operated in the second operating state is greater than the second predetermined period of time tα2 (such as about 2 seconds), and the variation ΔVO2R in the air-fuel ratio VO2R detected by the downstream O₂ sensor 37 is less than the predetermined value ΔVO2Rα, it may be determined that the downstream O₂ sensor 37 has failed. However, it is necessary to set the number of times of the determination to an appropriate value considering that the excessive number of times would lower the frequency of failure detection and the excessively small number of times would cause a wrong determination due to noises.

A description will now be given of a variation of the failure diagnosing process carried out by the failure diagnostic apparatus for the air-fuel ratio detecting device according to the present invention.

Figure 12:
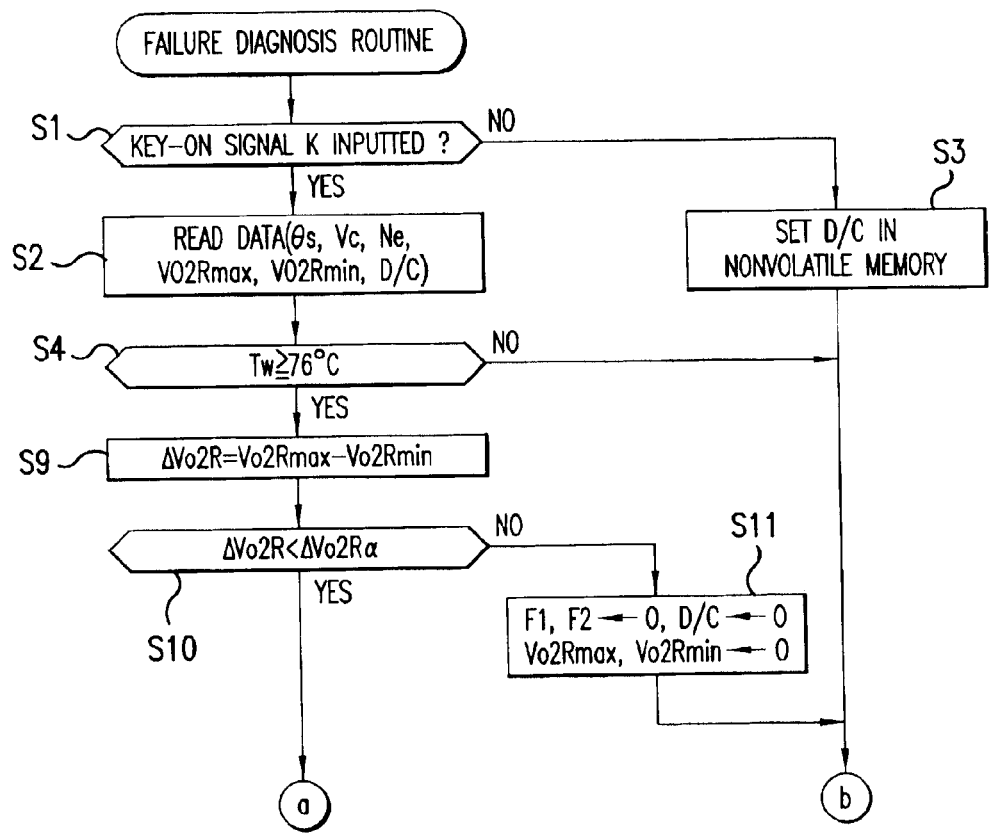
FIG. 12 is a flow chart showing a failure diagnosis routine executed by an engine controller according to a variation of the embodiment of the failure diagnostic apparatus for the air-fuel ratio detecting device shown in FIG. 1.
Figure 13A:
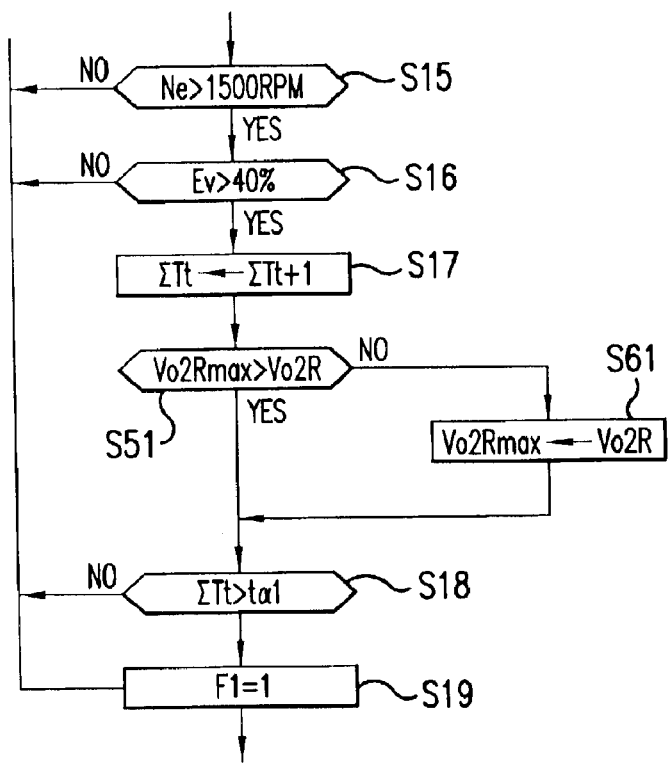
FIGS. 13A and 13B are flow charts showing the essential parts of a continued part of the failure diagnosis routine of FIG. 12.
Figure 13B:
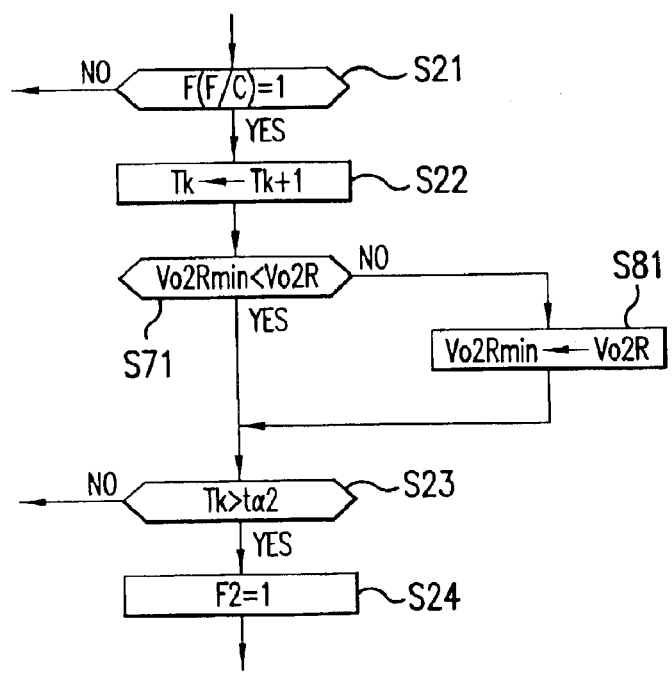

In the failure diagnosing process according to the variation, the failure diagnosis is carried out according to a failure diagnosis routine shown in FIGS. 12, 13A, and 13B. It should be noted that FIGS. 13A and 13B only show different steps from those of the failure diagnosis routine shown in FIG. 7.

In the above described failure diagnosis routine shown in FIGS. 6 and 7, the maximum value VO2Rmax and the minimum value VO2Rmin of the air-fuel ratio VO2R detected by the downstream O₂ sensor 37 is constantly updated. Specifically, every time the failure diagnosis routine is executed, it is determined whether the newest air-fuel ratio VO2R is greater than the stored maximum value VO2Rmax or not, or whether the air-fuel ratio VO2R is less than the stored minimum value VO2Rmin or not, irrespective of the operating state of the engine 1. If the newest air-fuel ratio VO2R is greater than the maximum value VO2Rmax or less than the minimum value VO2Rmin, the maximum value VO2Rmax or the minimum value VO2Rmin is updated to the newest air-fuel ratio VO2R and stored.

On the other hand, in the failure diagnosis routine according to the variation, the maximum value (the richest air-fuel ratio) of the air-fuel ratios VO2R, which are outputted by the downstream O₂ sensor 37 after it is determined in Steps S14 to S16 that the engine 1 is operated in the first operating state (such as Vc> about 30 km/h, Ne> about 1500 rpm, and Ev> about 40%) until the total period of time in which the engine 1 is operated in the first operating state exceeds the first predetermined period of time tα1, is stored. Further, the minimum i.e. the value (the leanest air-fuel ratio) of the air-fuel ratios VO2R, which are outputted by the downstream O₂ sensor 37 after it is determined in Step S21 that the engine 1 is operated in the second operating state (the fuel cut operating state) until the duration of the second operating state exceeds the second predetermined period of time tα2, is stored.

As shown in FIG. 13A, if it is determined in Steps S14 to S16 that the vehicle speed is equal to or greater than about 30 km/h, the engine speed Ne is greater than about 1500 rpm, and the cylinder charging efficiency Ev is greater than about 40%, it is then determined that the engine 1 is being operated in the first operating state, and the process proceeds to Step S17. In Step S17, the counter value ΣTt of the counter C (ΣTt) is incremented by 1 to measure the total period of time in which the engine 1 is operated in the first operating state.

In Step S51, it is determined whether the maximum output value VO2Rmax stored at the present moment in the storage section 202 is greater than the newest air-fuel ratio VO2R detected by the downstream O₂ sensor 37. If the maximum output value VO2Rmax stored at the present moment in the storage section 202 is greater than the newest air-fuel ratio VO2R detected by the downstream O₂ sensor 37, the process proceeds to Step S61 wherein the maximum output value VO2Rmax is updated to the newest air-fuel ratio VO2R, and the process proceeds to Step S18.

In Step S18, it is determined whether the counter value ΣTt of the counter C (ΣTt), i.e., the total period of time in which the engine 1 is operated in the first operating state is longer than the first predetermined period of time tα1 (such as about 10 seconds) or not. If it is determined that the counter value ΣTt of the counter C (ΣTt) is longer than the first predetermined period of time tα1, the first flag F1 is set to 1 in Step S19, and the process proceeds to Step S20.

Further, as shown in FIG. 13B, it is determined in Step S21 whether the fuel cut flag F (F/C) set in Steps B3 and B5 of the air-fuel ratio control routine shown in FIG. 9 is 1 or not. If it is determined that the fuel cut flag F (F/C) is 1, i.e., the operation range of the engine 1 lies in the fuel cut operation range and the engine 1 is operated in the second operating state, the process proceeds to Step S22 wherein the counter value Tk of the counter C (Tk) is incremented by 1 to measure the duration the engine 1 is continuously operated in the second operating state.

In the next Step S71, it is determined whether the minimum output value VO2Rmin stored at the present moment in the storage section 202 is less than the newest air-fuel ratio VO2R or not. If the newest air-fuel ratio VO2R is less than the present minimum output value VO2Rmin, the minimum output value VO2Rmin is updated to the newest air-fuel ratio VO2R, and the process proceeds to Step S18. Incidentally, if the maximum output value VO2Rmax or the minimum output value VO2Rmin is updated in Step S61 or S81, the updated maximum output value VO2Rmax or minimum output value VO2Rmin is stored in the storage section 202.

In Step S23, it is determined whether the counter value Tk of the counter C (Tk), i.e., the duration of the second operating state is greater than the second predetermined period of time tα2 (such as about 2 seconds) or not. If it is determined that the counter value Tk of the counter C (Tk), i.e. the duration of the second operating state is greater than the second predetermined period of time tα2, the second flag F2 is set to 1 in Step S24.

The difference ΔVO2R between the maximum output value VO2Rmax updated according to the air-fuel ratio VO2R detected while the engine 1 is operated in the first operating state and minimum output value VO2Rmin updated according to the air-fuel ratio VO2R detected while the engine 1 is operated in the second operating state in the about-mentioned manner is calculated in Step S9 of FIG. 12.

Then, after the completion of warm-up at a water temperature of about 76° C. or greater, the difference between the maximum output value VO2Rmax detected while the engine 1 is operated in the first operating state and the minimum output value VO2Rmin detected while the engine 1 is operated in the second operating state is calculated as the variation ΔVO2R in the air-fuel ratio VO2R detected by the downstream $O_2$ sensor 37, the total period of time ΣTt in which the engine 1 is operated in the first operating state (Vc> about 30 km/h, Ne> about 1500 rpm, and Ev> about 40%) is measured by the counter C (ΣTt), and the duration Tk the engine 1 is continuously operated in the second operating state (the fuel cut operating state) is measured by the counter C (Tk). If it is then determined that the total period of time ΣTt in which the engine 1 is operated in the first operating state is greater than the first predetermined period of time tα1 (such as about 10 seconds), the duration Tk the engine 1 is continuously operated in the second operating state is greater than the second predetermined period of time tα2 (such as about 2 seconds), and the variation ΔVO2R in the air-fuel ratio VO2R detected by the downstream $O_2$ sensor 37 is less than the predetermined value ΔVO2Rα, a failure of the downstream $O_2$ sensor 37 is ascertained once. Thereafter, if the failure determination frequency counter C (D/C) counts the malfunctioning of the downstream $O_2$ sensor 37 three times, it is then determined that the downstream $O_2$ sensor 37 has failed or deteriorated.

Incidentally, if the engine 1 is intermittently operated in the first operating state from the time point t2 to t3 and from the time point t4 to t5 of FIGS. 3A and 3D, the maximum output value VO2Rmax of the air-fuel ratios VO2R, which are outputted in the total period of time ΣTt in which the engine 1 is intermittently operated in the first operating state, is detected. Therefore, it is possible to accurately detect the air-fuel ratio VO2R even if the engine 1 is operated intermittently, not continuously, in the first operating state, and to increase the frequency of failure diagnosis, thus improving the response to detection and realizing rational failure diagnosis.

Although in the above described embodiment, it is determined whether the downstream $O_2$ sensor 37 disposed in the vicinity of the downstream end of the upstream catalyst 19 has failed or not, the present invention is not limited to this, but it may be determined whether an $O_2$ sensor disposed in the upstream catalyst 19 has failed or not.

Further, although in the above described embodiment, the failure determination frequency counter C (D/C) counts the malfunctioning of the downstream $O_2$ sensor 37 while the vehicle is at a standstill, the present invention is not limited to this. For example, if it is determined that the total period of time ΣTt in which the engine 1 is operated in the first operating state is longer than the first predetermined period of time tα1 and the duration Tk the engine 1 is continuously operated in the second operating state is longer than the second predetermined period of time tα2, and if it is determined that the variation ΔVO2R in the air-fuel ratio detected by the downstream $O_2$ sensor 37 is less than the predetermined value ΔVO2Rα, the failure determination frequency counter C (D/C) may count the malfunctioning of the downstream $O_2$ sensor 37 without waiting for the vehicle to come to a standstill.

Further, if there is the necessity of carrying out failure diagnosis as to the upstream $O_2$ sensor 36 disposed in the vicinity of the upstream end of the upstream catalyst 19, the failure diagnosis may be carried out in such a known manner as disclosed in Japanese Laid-Open Utility Model Publication (Kokai) No. 4-109445 for example, that the air-fuel ratio of an air-fuel mixture gas is forced to fluctuate and the air-fuel ratio VO2F outputted by the upstream $O_2$ sensor 36, and whether or not the upstream $O_2$ sensor 36 has deteriorated or failed is determined according to whether both duty ratios correspond or not. Incidentally, although the first predetermined period of time and the second predetermined period of time are the period of times in which the engine 1 is operated in the first operating state and the second operating state, respectively, the present invention is not limited to this, but the first predetermined period of time and the second predetermined period of time may be replaced by the number of cycles (a period of time) in which the engine 1 is operated in the first or second operating state.

As described above, according to the present invention, it is ascertained that the engine 1 has been operated in the first operating state for a longer period of time than the first predetermined period of time so that the air-fuel ratio detected by the air-fuel ratio detecting device disposed in the vicinity of the exhaust emission purifying device can surely be rich, and it is ascertained that the engine 1 has been operated in the second operating state for a longer period of time than the second predetermined period of time so that the air-fuel ratio detected by the air-fuel ratio detecting device can surely be lean. Therefore, whether the air-fuel ratio detecting device has failed or cannot be determined accurately according to the difference between the maximum output value and the minimum output value found by the air-fuel ratio detecting device, without being affected by the oxygen occluding condition inside the exhaust emission purifying device.

Further, the maximum output value and the minimum output value can be detected accurately in the state in which exhaust in the vicinity of the air-fuel ratio sensor is not affected by the oxygen occluding condition inside the exhaust emission purifying device, and even if the first operating state does not is continuously operated, the maximum output value can be found within the total period of time in which the engine 1 is intermittently operated in the first operating state. Specifically, the air-fuel ratio becomes richer in the first operating state, and furthermore, since the maximum output value is appears at the initial stage of transition in many cases and the period of time in which the engine 1 is operated in the first operating state is totaled, a large number of maximum values outputted from the sensor can be sampled even if the engine 1 is operated for only a short period of time. This makes the maximum output value more accurate. Moreover, the frequency of failure diagnosis can be increased sufficiently. Further, exhaust in the vicinity of the air-fuel ratio sensor becomes leaner as the internal combustion engine is continuously operated in the second operating state, and thereafter, the air-fuel ratio outputted from the air-fuel ratio sensor is fixed at a lean air-fuel ratio. Since it is determined that the engine 1 is operated in the second operating state by ascertaining that the duration the second operating state continues, not the total period of time in which the engine 1 is operated in the second operating state, has exceeded the predetermined period of time, the output value from the air-fuel ratio sensor can surely be lean in the second operating state.

Although in the above described embodiment, the difference between the maximum output value and the minimum output value of the detected air-fuel ratios is calculated as the variation in the air-fuel ratio, the present invention is not limited to this. The variation in the air-fuel ratio may be calculated based on information related to the air-fuel ratio other than the maximum output value and the minimum output value. In this case, if it is determined that the engine 1 has been operated in the first operating state for a longer period of time than the first predetermined period of time and has been operated in the second operating state for a longer period of time than the second predetermined period of time, and if the variation in the air-fuel ratio is equal to or less than a predetermined value, it is then determined that the air-fuel ratio sensor has failed.

It should be understood that there is no intention to limit the invention to the specific forms disclosed, but on the contrary, the invention is to cover all modifications, alternate constructions, and equivalents falling within the spirit and scope of the invention as expressed in the appended claims.

What is claimed is:

1. A failure diagnostic apparatus for air-fuel ratio detecting device, comprising:
    an exhaust emission purifying device provided in an exhaust passage of an internal combustion engine;
    an air-fuel ratio detecting unit that detects an air-fuel ratio of an exhaust gas from said exhaust emission purifying device;
    a first determination unit that determines that the internal combustion engine has been operated in a first operating state, in which an air-fuel ratio of the exhaust gas in a vicinity of said exhaust emission purifying device is estimated to be rich, for a period of time longer than a first predetermined period of time;
    a second determination unit that determines that the internal combustion engine has been operated in a second operating state, in which an air-fuel ratio of the exhaust gas in a vicinity of said exhaust emission purifying device is estimated to be lean, for a period of time longer than a second predetermined period of time;
    an air-fuel ratio variation calculating unit that calculates a variation in the air-fuel ratio outputted from said air-fuel ratio detecting unit until said first determination unit and said second determination unit make the determinations; and
    a failure diagnosis device that determines that said air-fuel ratio detecting unit has failed if said first determination unit and said second determination unit make the determinations and if it is determined that the variation in the air-fuel ratio calculated by said air-fuel ratio variation calculating unit is less than a predetermined value.

2. A failure diagnostic apparatus for air-fuel ratio detecting device according to claim 1, wherein the internal combustion engine is estimated to be operated in the first operating state based on a load on the internal combustion engine.

3. A failure diagnostic apparatus for air-fuel ratio detecting device according to claim 1, wherein the internal combustion engine is estimated to be operated in the second operating state based on a fuel cut operation by the internal combustion engine.

4. A failure diagnostic apparatus for air-fuel ratio detecting device according to claim 1, wherein said first determination unit makes the determination when a total period of time in which the internal combustion engine has been operated in the first operating state exceeds the first predetermined period of time.

5. A failure diagnostic apparatus for air-fuel ratio detecting device according to claim 1, wherein said second determination unit makes the determination when a period of time in which the internal combustion engine has been continuously operated in the second operating state exceeds the second predetermined period of time.

6. A failure diagnostic apparatus for air-fuel ratio detecting device according to claim 1, wherein said air-fuel ratio variation calculating unit includes, an air-fuel ratio storage unit that stores the air-fuel ratios detected and outputted by said air-fuel ratio detecting unit until said first determination unit and said second determination unit make the determinations or air-fuel ratio information acquired based on the detected air-fuel ratios, and calculates a variation in the detected air-fuel ratio based on the detected air-fuel ratios or the air-fuel ratio information stored in said air-fuel ratio storage unit.

7. A failure diagnostic apparatus for air-fuel ratio detecting device according to claim 6, wherein
    said air-fuel ratio storage unit stores a richest air-fuel ratio detected and outputted by said air-fuel ratio detecting unit, and a leanest air-fuel ratio detected and outputted by said air-fuel ratio detecting unit; and
    said air-fuel ratio variation calculating unit calculates a variation in the detected air-fuel ratio according to a difference between the richest air-fuel ratio and the leanest air-fuel ratio.

8. A failure diagnostic apparatus for air-fuel ratio detecting device according to claim 6, wherein
    said air-fuel ratio storage unit stores a richest air-fuel ratio detected and outputted by said air-fuel detecting unit when the internal combustion engine is operated in the first operating state, and
    said air-fuel ratio variation calculating unit calculates a variation in the air-fuel ratio based on the richest air-fuel ratio detected in the first operating state.

9. A failure diagnostic apparatus for air-fuel ratio detecting device according to claim 6, wherein
    said air-fuel ratio storage unit stores a leanest air-fuel ratio detected and outputted by said air-fuel ratio detecting unit when the internal combustion engine is operated in the second operating state, and
    said air-fuel ratio variation calculating unit calculates a variation in the air-fuel ratio based on the leanest air-fuel ratio detected in the second operating state.

10. A failure diagnostic apparatus for air-fuel ratio detecting device according to claim 1, further comprising:
    an operation determination resetting unit that determines whether the variation in the air-fuel ratio calculated by said air-fuel ratio variation calculating unit is equal to or greater than the predetermined value, and resetting the determinations made by said first determination unit and said second determination unit if it is determined that the variation is equal to or greater than the predetermined value.

11. A failure diagnostic apparatus for air-fuel ratio detecting device according to claim 1, wherein said air-fuel ratio detecting device is disposed downstream of said exhaust emission purifying device in the exhaust passage.

* * * * *